US011213607B2

(12) United States Patent
Grover et al.

(10) Patent No.: US 11,213,607 B2
(45) Date of Patent: Jan. 4, 2022

(54) CELL PURIFICATION AND DELIVERY USING SHEAR THINNING GEL

(71) Applicant: The University of Birmingham, Birmingham (GB)

(72) Inventors: Liam Grover, Birmingham (GB); Paula Mendes, Birmingham (GB); Richard Williams, Birmingham (GB)

(73) Assignee: THE UNIVERSITY OF BIRMINGHAM, Edgbaston Birmingham (GB)

( * ) Notice: Subject to any disclaimer, the term of this patent is extended or adjusted under 35 U.S.C. 154(b) by 0 days.

(21) Appl. No.: 16/060,877

(22) PCT Filed: Dec. 9, 2016

(86) PCT No.: PCT/GB2016/053883

§ 371 (c)(1),
(2) Date: Jun. 8, 2018

(87) PCT Pub. No.: WO2017/098258

PCT Pub. Date: Jun. 15, 2017

(65) Prior Publication Data

US 2019/0009000 A1 Jan. 10, 2019

(30) Foreign Application Priority Data

Dec. 10, 2015 (GB) ..................................... 1521784

(51) Int. Cl.

| | |
|---|---|
| ***A61L 27/20*** | (2006.01) |
| ***A61L 27/38*** | (2006.01) |
| ***H01J 49/00*** | (2006.01) |
| ***A61L 27/22*** | (2006.01) |
| ***A61L 27/24*** | (2006.01) |
| ***A61L 27/54*** | (2006.01) |
| ***C07K 1/22*** | (2006.01) |
| ***C07K 16/28*** | (2006.01) |
| ***A61L 27/46*** | (2006.01) |
| ***H01J 49/06*** | (2006.01) |
| *A61K 47/36* | (2006.01) |
| *A61K 47/42* | (2017.01) |
| *A61K 47/02* | (2006.01) |

(52) U.S. Cl.

CPC ............. *A61L 27/20* (2013.01); *A61L 27/222* (2013.01); *A61L 27/24* (2013.01); *A61L 27/3817* (2013.01); *A61L 27/3821* (2013.01); *A61L 27/3847* (2013.01); *A61L 27/3852* (2013.01); *A61L 27/3869* (2013.01); *A61L 27/46* (2013.01); *A61L 27/54* (2013.01); *C07K 1/22* (2013.01); *C07K 16/2896* (2013.01); *H01J 49/0018* (2013.01); *H01J 49/067* (2013.01); *A61K 47/02* (2013.01); *A61K 47/36* (2013.01); *A61K 47/42* (2013.01); *A61L 2300/256* (2013.01); *A61L 2400/06* (2013.01)

(58) Field of Classification Search

CPC .................................................. A61L 27/3817

See application file for complete search history.

(56) References Cited

U.S. PATENT DOCUMENTS

| | | | | |
|---|---|---|---|---|
| 5,639,620 A * | 6/1997 | Siiman | G01N 33/531 | 427/2.13 |
| 2004/0076685 A1* | 4/2004 | Tas | A61L 27/12 | 424/602 |
| 2006/0096504 A1 | 5/2006 | Grover et al. | | |
| 2007/0048288 A1 | 3/2007 | Lyu et al. | | |
| 2008/0089867 A1 | 4/2008 | Fernandes et al. | | |
| 2009/0291930 A1* | 11/2009 | Grover | A61K 9/143 | 514/180 |
| 2010/0215715 A1 | 8/2010 | Han et al. | | |
| 2013/0189230 A1 | 7/2013 | Shoichet et al. | | |
| 2015/0024411 A1 | 1/2015 | Stadler | | |

FOREIGN PATENT DOCUMENTS

| | | | |
|---|---|---|---|
| WO | 2003099347 | A1 | 12/2003 |
| WO | 2007027289 | A1 | 3/2007 |
| WO | 2009002456 | A2 | 12/2008 |
| WO | 2008006204 | A3 | 2/2011 |
| WO | 2011072399 | A1 | 6/2011 |
| WO | 2012149358 | A1 | 11/2012 |
| WO | 2014022939 | A1 | 2/2014 |
| WO | 2015154048 | A1 | 10/2015 |

OTHER PUBLICATIONS

Lee et al., Adv. Funct. Mater., 2014, 24:1538-1550.*
Hunt et al., J. Mater. Chem. B, 2014, 2:5319-5338.*
Camci-Unal et al., Soft Matter, 2010, 6(20):5120-5126 or pp. 1-15 as printed.*
Skardal et al., Adv. Mater., 2010, 22:14736-4740.*
Ballios BG et al., A hydrogel-based stem cell delivery system to treat retinal degenerative diseases, Biomaterials, Mar. 1, 2010, vol. 31, No. 9, pp. 2555-2564, Elsevier Science Publishers BV., Barking GB.
Grover, Liam et al., The effect of amorphous pyrophosphate on calcium phosphate cement resorption and bone degeneration, Biomaterials, Jun. 7, 2013, vol. 34, No. 28, pp. 6631-6637, Elsevier Science Publishers BV Barking GB.
International Search Report dated Jun. 15, 2018.
Jahromi, Shiva H. et al., Degradation of polysaccharide hydrogels seeded with bone marrow stromal cells, Mar. 22, 2011, Journal of the Mechanical Behavior of Biomedical Materials, vol. 4, No. 7, pp. 1157-1166, Elsevier, Amsterdam NL.

(Continued)

*Primary Examiner* — Bin Shen
(74) *Attorney, Agent, or Firm* — Gorman IP Law, APC

(57) ABSTRACT

The invention provides a cell binding composition comprising a shear thinning gel wherein the shear thinning gel having attached to it one or more cell selective binding agents, or the shear thinning gel having dispersed therein a plurality of gel beads, the gel beads having attached to them one or more cell selective binding agents.
Methods of enriching cells using the compositions and using the cells to treat injury or disease are also provided.

22 Claims, 4 Drawing Sheets

(56) References Cited

OTHER PUBLICATIONS

Yan, Congqi et al., Injectable solid hydrogel: mechanism of shear-thinning and immediate recovery of injectable [beta]-hairpin peptide hydrogels, Jan. 1, 2010, Soft Matter, vol. 6, No. 20, p. 5143.

* cited by examiner

CELL PURIFICATION AND DELIVERY USING SHEAR THINNING GEL

This application is the National Phase Under 35 USC § 371 of PCT International Application No. PCT/GB2016/053883 filed on Dec. 9, 2016, which claims priority under 35 U.S.C. § 119 on Patent Application No. 1521784.7 filed in the United Kingdom on Dec. 10, 2015, the entire contents of each of which are hereby incorporated by reference.

The invention relates to a cell binding composition comprising a shear thinning gel, the shear thinning gel having attached to it one or more cell-selective binding agents. Alternatively the shear thinning gel comprises a plurality of gel beads dispersed within the shear thinning gel, the gel beads having attached to them one or more cell-selective binding agents. Such gels are used to enrich cell populations from sources, such as bone marrow aspirate. They then may be used in a variety of medical and surgical treatments.

The avascular nature of cartilage and the low number of cells that are found within the matrix of articular cartilage means that following damage it is a tissue that has very little regenerative capacity. Cartilage damage to the knee is a common disorder, particularly in the young athletic population where the incidence has been reported to be as high as 36%. Cartilage damage left untreated negatively affects daily living, recreational and professional activities, as well as quality of life, predisposing patients to the development of osteoarthritis, a major cause of disability that poses a significant socioeconomic burden. Current therapies have failed to provide a consistent durable repair, with ACI cell therapy (Autologous Chondrocyte Implantation) currently the most effective. Stem cell therapies have the potential to revolutionise current treatments for damaged cartilage, however, their impact to-date has been limited. The delivery of autologous cells derived from bone marrow aspirated by the surgeon in a one stage procedure has shown some success, however, since the cell population is heterogeneous, with low MSC numbers, it can result in the formation of an inferior fibro cartilaginous structure. Some researchers have sought to avoid this by sorting cell populations harvested from the patient according to cell surface markers and isolating those that are associated with improved chondrogenesis. Although this approach has shown promise, as the cells are processed away from the operating theatre, they are classified as an Advanced Therapy Medicinal Product (ATMP) by the European Medicines Agency (EMA). ATMPs are processed in strictly controlled Good Manufacturing Practice (GMP) facilities. The limited number of GMP cell therapy facilities that are available Europe-wide and the increased cost of cell processing means that they are unlikely to be widely adopted by national health providers across the EU.

The use of cell carrier systems in general is known to use a carrier medium, such as a liquid containing a polymer to carry cells, for example in suspension. The suspended cells are placed at the site of a wound or a place where cell replacement is needed, and the cells help with the treatment being carried out. WO 03/099347, for example, describes a cell carrier system using a liquid which is selected to have a specific gravity or density within a range of specific gravities or densities which matches those of a selected cell type. This allows cells to be suspended within the media.

The use of a variety of polymer based delivery systems is generally known. WO 2007/027289, for example, describes shear thinning polymers. They are used to administer cells when the cells are delivered to a site of use. Poly (alkylene oxide) gels are exemplified. The use of hylauronan, alginates and methylcellulose, shear thinning gels as cell delivery systems is described in US 2013/0189230. Pre-purified cells are suspended within the polymer gel and injected into place. The gels may be derivatised to attach proteins with useful biological activities to the polymers. WO 2012/149358 also describes polymer based hyrdogels such as methacrylate, alginates, gelatin and collagen and mixtures thereof. Compounds or cells are suspended within the deformable matrix of the polymers and are used in surgery.

US 2010/0215715 describes similar injectable, precast, beads or micelles of gels which are used to encapsulate cells.

WO 2014/022939 A describes a hydrogel containing a patient's own cells which can be prepared at the bed side. The use of bone marrow aspirate is discussed as a potential source of cells, without further purification of the cells. Cells are typically incorporated into partially gelled hydrogels as a suspension within the gel.

Shear thinning gels have a higher viscosity at rest and decreased viscosity when subject to shear, for example when passed through a needle. It is believed that the polymers that make such gels typically have molecules or particles that are entangled at rest and then become disentangled when a shear force is applied to the gels. This results in the decreased viscosity observed. Shear force may, for example, be the stirring or pumping or flow of the gel. For example, the shear rate may change from 1 $s^{-1}$ to 1000 $s^{-1}$ for cell delivery.

The inventors have realised that the properties of shear thinning gels or gel beads dispersed within the shear thinning gel, could be utilised, not only as a delivery medium for cells, but also used to enrich cells from the source of cells. This potentially allows cells to be enriched, for example, at the hospital or other treatment centres where a patient is being treated.

A first aspect of the invention provides a cell binding composition comprising a shear thinning gel, the shear thinning gel comprising a plurality of gel beads dispersed within the shear thinning get, the gel beads having attached to them one or more cell selective bindings agents.

The shear thinning gel enables delivery of an enriched population of cells attached to the gel beads by exhibiting fluid-like properties upon application of shear force, such as injection through a needle, which decreases the viscosity of the system. The shear thinning gel also retains the enriched population of cells when the shear force is removed, for example to help retain the cells at the wound site. This simplifies the enrichment of cells and delivery to the wound site.

A second aspect of the invention provides a cell binding composition comprising a shear thinning gel, the shear thinning gel having attached to it one or more cell-selective binding agents. In this embodiment the cells are bound to the shear thinning gel itself.

The cell-selective binding agents may be covalently attached to the shear thinning gel molecules or gel beads or indeed both. The attachment or cross-linking of, for example, protein-based binding agents to polymers is generally known in the art. For example, US 2013/0189230 describes a number of ways of attaching functional peptides or proteins to gels such as alginate. These include the use of, for example, carbodiimide coupling.

The cell selective binding agent is typically a moiety to which a predefined cell of interest can bind. This means that, for example, the population of a cell may be enriched by mixing the composition with a source of cells, such as for example blood or bone marrow aspirate, allowing the cells of interest to bind to the shear thinning gel via the cell selective binding agent, and washing unbound material away from the composition.

For example NHS-EDC (N-hydroxysuccinimide)-(1-ethyl-3C3-dimethylamino propylcarbodiimide. HCl) may be used to attach proteins to the gels. The hydroxyl or carboxyl groups on gels such as alginate may be modified to allow cell-selective binding agents to bind to the gel beads and/or shear thinning gel.

The addition of amine groups to alginate is also known in the art. This may be used to allow, for example, the attachment of binding agents such as antibodies. Silanes such as APTES (3-Aminopropyl)triethoxysilane) may also be coupled to the gel to provide attachment sites for the binding agents.

The cell binding agent may, for example, be an antibody or fragment thereof specific for a protein or other marker found on the surface of the cells of interest. Alternatively, the cell selective binding agent may be a receptor or fragment thereof, capable of binding a molecule found on the surface of the cell of interest.

For example, the cell selective binding agent may be capable of selectively binding to stem cells, such as bone marrow stem cells (typically non-embryonic stem cells), smooth muscle cells, hepatocytes, epithelial cells, fibroblasts, osteocytes, chondrocytes or blood platelets.

The cells may be allogeneic, autologous or xenogeneic, most typically autologous cells.

Cells are typically mammalian, for example, horse, sheep, cow, pig, rat, mouse, rabbit most typically human cells.

Typically the cells are osteocyte, chondrocyte or blood platelets. Osteocytes are useful for the encouraging of bone regrowth in damaged bone. Chondrocytes are especially useful in the treatment or repair of cartilage. Blood platelets may be used for a range of purposes, for example, such as those described in US 2008/0089867, which describes obtaining concentrated platelets by centrifuging blood from patients. Platelets may be used to increase the survival of other transplanted cells.

Accordingly, a further aspect of the invention provides that the cell binding composition comprises shear thinning gels having two or more different cell selective binding agents. This allows the composition to have two or more different cells bound to the gels. The individual gel molecules may have two or more different cell selective binding agents attached to the molecule, or a mixture of two gels with different binding agents may be used. Alternatively, the cell may be attached to one batch of the gels, and a second cell attached to a different batch of gels, each containing different cell selective binding agents. The two batches containing the different cells may then be mixed together.

Most typically, the cell of interest is a chondrocyte, and the cell selective binding agent is an antibody or fragment thereof capable of specifically binding CD34. CD34 protein is an adhesion molecule that is selectively expressed in a number of different cells. Cells expressing CD34 are normally found in the umbilical cord and bone marrow as hematopoiteic cells, a subset of mesenchymal stem cells, endothelial progenitor cells, endothelial cells of blood vessels, mast cell, some dendritic cells, and chondrocytes. Accordingly, if for example bone marrow is extracted and mixed with the shear thinning gels then a number of different cells, including chondrocytes will bind to the gel. This means that the chondrocytes will be enriched, compared to the original bone marrow extract.

Other markers include CD29, CD44, CD73, CD105, CD271.

CD29 is a cell adhesion molecule and BMSC cells expressing it have improved chondrogenic differentiation. CD44 is a family of cell adhesion molecules found on bone-marrow stem cells. CD73 is an enzyme which converts AMP to adenosine and is found in high concentrations during chondrogenic induction. CD105 is a type 1 membrane glycoprotein. $CD105^+$ cells display enhanced chondrogenic potential. CD 271 is a transmembrane protein of the TNF super family. $CD271^+$ BMSC cells have the capability of chondrogenic differentiation.

The composition may additionally comprise calcium pyrophosphate particles dispersed within the composition. Typically the calcium pyrophosphate particles are amorphous or substantially star shaped. Such particles are described in, for example, US 2006/0096504 and WO 2008006204 A2, which are incorporated by reference in their entirety. They are especially useful for encouraging bone growth. They may especially be used in combination with, for example, gels with a cell selective binding agent for osteocytes. Alternatively the combination of gel and calcium pyrophosphate may be used without cells.

The calcium phosphate particles are typically 100 nm to 1 micron diameter, more typically 1 micron to 10 nm-5 microns, or 1 nm-100 micron diameter. They may be fibrous or star shaped, amorphous or crystalline.

The invention also provides a shear thinning gel comprising calcium phosphate, especially calcium pyrophosphate, particles dispersed within the composition and optionally one or more antibiotics. Such material may be used as a bone repair or defect filling material. It assists in stabilising bone fracture sites; provide conduits for new bone growth; the calcium phosphate stimulates bone growth; the gel maintains antibiotic (where present) at the site to reduce infection. The gel and calcium phosphate may be as described elsewhere for other aspects of the invention. Cells, where present, may include osteocytes.

The antibiotic may be any suitable antibiotic, for example, antibacterial, antiviral or antifungal agent generally known in the art. Examples include, beta-lactams (e.g. penicillins, cephalosporins, monobactams, carbapanums), macrolides such as erythromycin, aminoglycosides such as kanamycin, neomycin and streptomycin, and tetracyclines.

The shear thinning gel and/or gel beads used in any aspect of the invention may be selected from alginate, gellan gum, gelatin and collagen. Other polymers that may be used include poly (alkylene oxide) such as poly(ethylene oxide) and poly(ethylene-co-propylene oxide), and carboxymethyl cellulose. This shear thinning gel may be the same or different to the gel beads. The gel beads may comprise, for example, a higher concentration of the gel that the shearing gel.

Typically the composition comprises a bio-compatible buffer.

The composition may comprise one or more additional bioactive compounds such as growth factors including platelet derived growth factor (PDGF), vascular endothelial growth factor (VEGF), epidermal growth factor (EGF), insulin-like growth factor (IGF), bone morphogenic protein and transforming growth factor (TGF-β). Other compounds include cytokines and extra-cellular matrix proteins such as collagens, elastins, fibronectin, fibrinogen, fibrin and laminin.

The composition may comprise anti-inflammatory compounds, analgesics, anti-bacterial or anti-fungal agents generally known in the art.

Typically shear thinning gels comprise 0.01 to 5%, especially 0.1 to 3% wt/vol in a solvent, such as water. Typically divalent cations are used with, for example, alginate, to cross link the polymers used. Divalent cations include $Ca^{2+}$, $Mn^{2+}$, $Mg^{2+}$, $Fe^{2+}$, $Cr^{2+}$, $Zn^{2+}$, $Sr^{2+}$, and $Cu^{2+}$ in typically 0.1M-2M solutions. Typically 9 ml dissolved polymer is added 1 ml of cross linker cation solution.

1% wt/vol or 2% wt/vol alginate may be used in water with 1M $CaCl_2$ solution at a volume/volume ratio of 10;1. The $CaCl_2$ may be replaced with, for example, 0.25M $MnSO_4$ or $MnCl_2$.

The gel beads may use, for example, higher concentrations of gel polymer or cross linker to form denser beads than the surrounding shear thinning gel.

Typically beads are formed by dropping the gel into a solution of cross linking agent, to form the beads.

Typically 0.01 to 0.5% v/v, especially 0.1 to 0.25% v/v beads to shear thinning gel is used.

The gel, such as alginate, may have been treated, for example, by subjecting to shear forces, such as using a shear stirrer prior to contacting with cells to introduce shear thinning properties of the material.

The shear thinning gels may be produced using, for example, a rheometer with a rotor, such as having rotary vane geometry. A pin stirrer may also be used.

Additional bioactive compounds, such as cell growth media to maintain the cells or compounds capable of inducing a response, such as bone morphogenic protein or an angiogenic protein, or antimicrobial compounds may also be provided within the or each gel.

A further aspect of the invention provides a composition according to the invention comprising one or more cells bound to the gel.

Purification columns and syringes comprising the compositions of the invention are also provided. For example, the gel may be enclosed within a column through which a sample, such as bone marrow extract, is passed through. Cells in the sample bind to the gel and unbound cells and material is washed through the gel, prior to recovery of the gel for further use.

The invention further provides methods of enriching a population of cells comprising providing composition or column according to the invention, contacting a sample containing the cells with the composition, allowing cells to bind to the composition, and removing unbound sample and materials from the composition.

A further aspect provides:

a method of enriching a population of cells comprising:

(i) providing a gel, the gel having attached to one or more cell selective agents or providing a gel having dispersed therein a plurality of gel beads, the gel beads having attached to them one or more cell selective binding agents;

(ii) contacting a sample containing the cells with the gel;

(iii) allowing the cells to bind to the gel or beads dispersed therein; and (iv) removing unbound cells from the gel or beads dispersed therein; preferably wherein the gel is selected from alginate, gellan gum, gelatin or collagen.

The sample may, for example, comprise blood, plasma, serum or bone marrow. The cells and components may be as defined above.

Methods of treating a patient comprising the use of the compositions of the invention is also provided. The method may be used, for example, for the treatment of tendon, collagen, bones, cartilage, burns, scarring, cornea injury, wounds or other illnesses.

The compositions may be applied to an area where the cells are needed via, for example, pipette, syringe, needle, a cream or ointment such as a topical cream or ointment, injection or spray. The enriched gel has low viscosity whilst under shear and being applied, then once in place the gel is no longer under shear forces and sets in situ. This helps keep the cells and other compounds of interest in place at the site where they are needed.

The invention will now be described by way of example only with reference to the following figures:

FIG. 1: Visual demonstration of the shear-thinning properties of an example formulation, making reference to the viscosity-shear rate profile (C). At rest, the system has shape maintaining properties even under inversion (A). Upon application of shear force, by shaking in this example, the system reduces in viscosity and gains the ability to flow out of its container (B). The viscosity profile of toothpaste is displayed to put the measured viscosity data of the example formulation in to everyday context FIG. 2: Photo showing the example gel formulation being poured from a container immediately after shaking (A). One of the gel beads is highlighted to demonstrate the cell-binding agents bound to the surface. For demonstration purposes, the bead surface was engrafted with a CD34 antibody (the cell binding agent) incorporating a green fluorescent label. (B) shows how the surface of the highlighted bead is covered in green fluorescence indicating coverage with the CD34+ antibody. After mixing with bone marrow aspirate and removal of unbound cells, the surface of a bead is shown to be partially covered with CD34+ cells (red) (C).

FIG. 3: This second example formulation depicts the calcium pyrophosphate star particles dispersed into the shear-thinning gel instead of gel beads in order to demonstrate the ability to deliver non-cell based therapeutic agents. The shear gel formulation in this example uses the same manufacture process as described in FIG. 2, but with $Mn^{2+}$ ions (0.25M manganese sulfate in deionised water) used as the crosslinking agent. At rest the shear-thinning gel containing the star particles behaves as a monolith and maintains shape (A). (B) shows the a portion of the gel system shown in (A) loaded into a 10 mL syringe. Upon injection through the syringe, the star particle containing gel flows out of the syringe and can be extruded on to a surface (C,D). The extruded star particle containing gel thickens almost immediately after injection, remains in position even after inversion (E) and can be cleaved into portions (F,G). Only after repeated forceful impact against the work surface is the extruded gel moved around the dish (H).

FIG. 4: Micro X-Ray Fluorescence maps of a 10 mm×6 mm portion (A) of an example formulation containing calcium pyrophosphate star particles, demonstrating even dispersion across a large area of gel. Locations containing calcium pyrophosphate were identified by mapping the presence of calcium (B) and phosphorous (C), with both maps overlaid (D). (E) shows how the star particles detected in (B) and (C) co-localise with the star-particles observed directly in the light microscope image of the same area (A).

SHEAR GEL PRODUCTION 18 ml 2% wt alginate in deionised water was added to a shear stirrer. This was warmed to 60° C. before shear force is applied via a rotor. 2 mL of 0.1M calcium chloride was added drop wise to the heated alginate solutions. The shear rate used was 450 $s^{-1}$.

Alginate Bead Solution

4% wt alginate in deionised water at 60° C. was prepared. This was added drop wise through a hypodermic syringe into 1M calcium chloride in a beaker to form beads.

Gel beads were mixed into shear thinning gel at 0.1 to 0.25 v/v.

Calcium Pyrophosphate Gels

Shear gels were prepared as described above, but 0.25M $MnSO_4$ was used as a cross linker.

The particles of calcium phosphate were made by first preparing 300 mM aqueous solution of calcium chloride and a 150 mM aqueous solution of Sodium pyrophosphate decahydrate. Both solutions were adjust to pH 7 by addition of appropriate amounts of 12M hydrochloric acid and 1M sodium hydroxide while monitoring pH with a pH meter. Equal volumes of the calcium chloride solution and sodium pyrophosphate solutions were mixed together (200 mL of each in this case) under vigorous stirring for 1 minute at room temperature before the stirring was stopped and the reaction left alone for 1 hour. Within this time, a white precipitate appears to separate from the water and this precipitate has a fibrous appearance upon closer examination by eye. The water is decanted off and fresh deionised water is added to resuspend the precipitate and left overnight. The final product is then extracted from the water by vacuum filtration and dried under ambient conditions to form a powder of calcium pyrophosphate star-shaped particles. Further details of the production of such particles is described in WO 2008006204 A2, which is incorporated by reference in its entirety.

Figure 1:
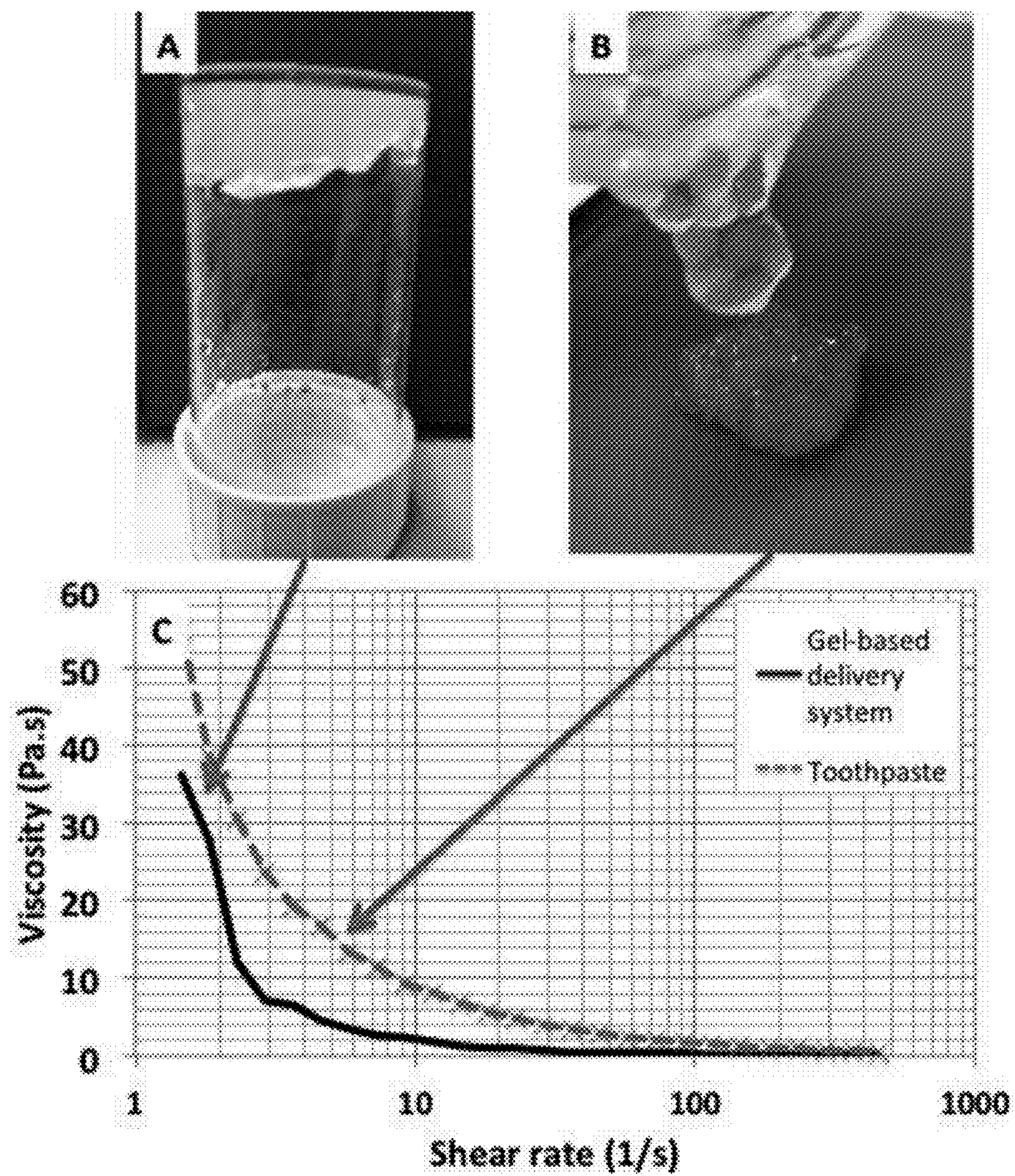
FIG. 1 shows the shear thinning properties of the formulation.
Figure 2:
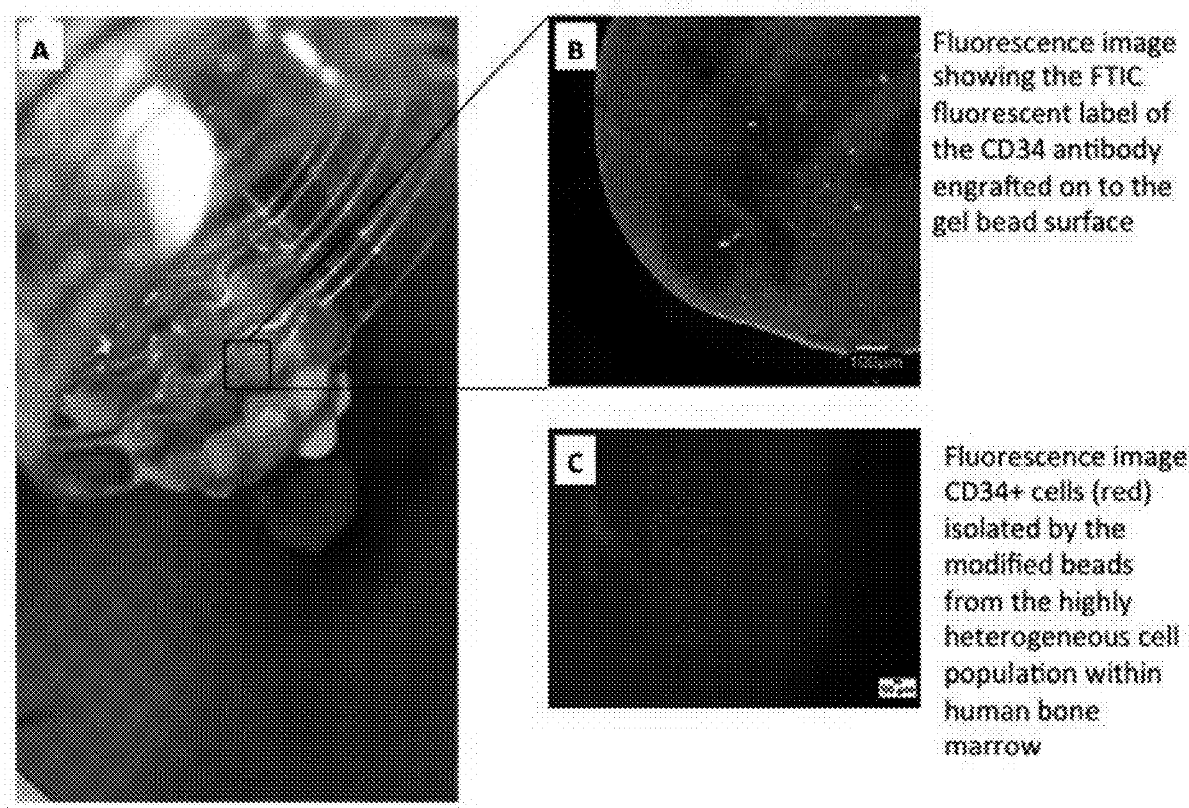
FIG. 2 shows beads engrafted with $CD34^+$ antibodies labelled with a green fluorescent label. (B) shows the beads glowing green with the labelled antibodies. (C) shows red labelled cells from bone aspirate attached to the beads vie the $CD34^+$ antibodies. This shows enrichment of the cells by the antibodies or the beads.
Figure 3:
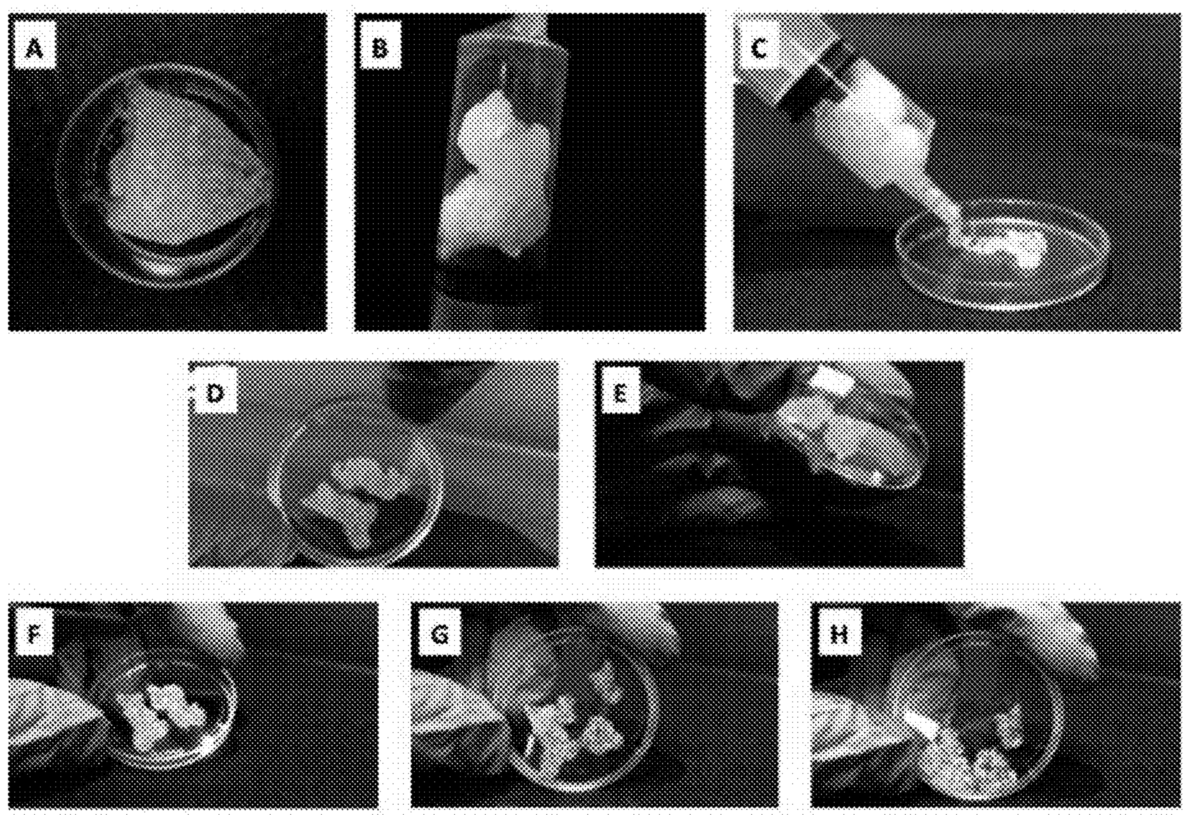

At rest the shear thinning gel contains star shaped calcium pyrophosphate particles and behaves as a monolith and maintains shape (FIG. 3A). When loaded into a syringe (FIG. 3B) it can be extruded onto a surface (FIG. 3 C, D). This thickens almost immediately even after inversion (FIG. 3 E) and can be cleaved (FIG. 3E, F). Repeated impacts allowed the gel to move around the dish (FIG. 3H).

Figure 4:
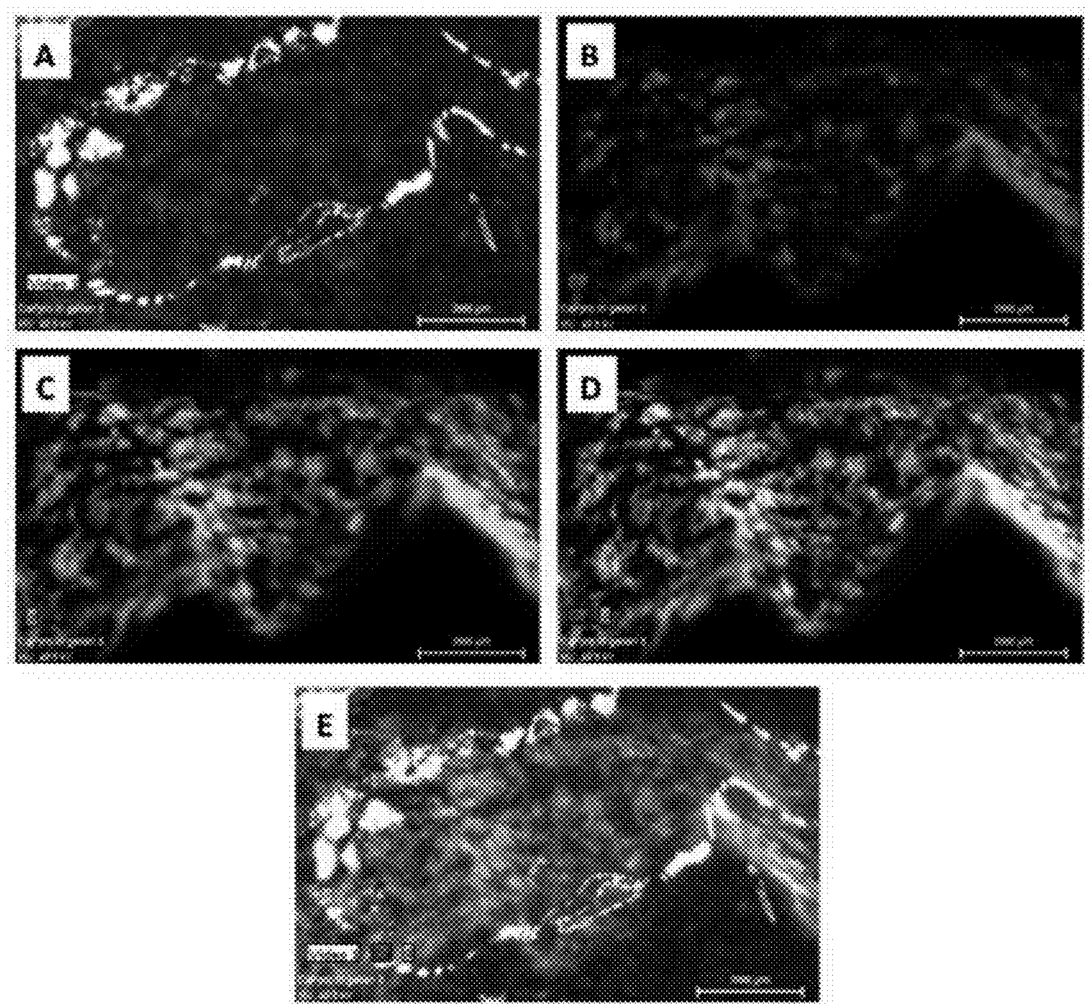

Cells may be added to the composition. Antibiotics may also be used with composition The dispersion of calcium pyrophosphate star particles is shown in FIG. 4.

The invention claimed is:

1. A cell binding composition comprising a shear thinning gel, wherein the shear thinning gel comprises a plurality of gel beads dispersed within the shear thinning gel, the gel beads having attached to them one or more cell selective binding agent, wherein the shear thinning gel and the gel beads are independently selected from the group consisting of alginate, gellan gum, gelatin, collagen, poly(alkylene oxide), poly(ethylene oxide), poly(ethylene-co-propylene oxide), or carboxymethyl cellulose.

2. A composition according to claim 1, wherein the cell selective binding agent is an antibody or receptor or a fragment thereof, capable of binding a predetermined antigen or ligand on a cell.

3. A composition according to claim 1, wherein the cell selective binding agent is capable of binding an osteocyte, chondrocyte or blood platelet.

4. A composition according to claim 1, wherein the cell selective binding agent is an antibody or fragment thereof which is capable of specifically binding CD34, CD29, CD44, CD73, CD105 or CD271.

5. A composition according to claim 1, additionally comprising calcium pyrophosphate particles dispersed within the composition.

6. A composition according to claim 5, wherein the calcium pyrophosphate particles are star shaped.

7. A composition according to claim 1, comprising one or more cells bound to the gel beads.

8. A delivery device comprising a composition according to claim 7.

9. The delivery device according to claim 8, wherein the delivery device is any one of a pipette, syringe, needle, spray delivery device, ointment, or cream.

10. The composition according to claim 7, wherein the one or more cells are allogenic, autologous, or xenogeneic.

11. A purification column comprising a composition according to claim 1.

12. A method of enriching a population of cells comprising providing a composition according to claim 1, contacting a sample containing the cells with the composition, allowing the cells to bind to the composition, and removing unbound samples from the composition.

13. A method according to claim 12, wherein cells bound to the composition are placed in a delivery device for delivery to a site to be treated in a patient.

14. A method according to claim 13, wherein the delivery device comprises a pipette, a syringe, a needle, a spray delivery device, an ointment or a cream.

15. A method according to claim 12, wherein the sample comprises blood, plasma, serum or bone marrow extract.

16. A method according to claim 12, wherein the cell is an osteocyte, chondrocyte or platelet.

17. A method according to claim 12, wherein the enriched cells are contacted with a site on a patient to be treated.

18. A method of treating a patient comprising administering to a patient in need thereof a therapeutically effective amount of a composition according to claim 1.

19. A method according to claim 18, wherein the method is a method of treating tendon, bone, cornea, cartilage or wound.

20. A bone repair composition comprising a shear thinning gel, wherein the shear thinning gel comprises a plurality of gel beads dispersed within the shear thinning gel, the gel beads having attached to them one or more cell selective binding agents and calcium pyrophosphate particles dispersed within the composition, and optionally one or more antibiotics.

21. A composition according to claim 20 comprising amorphous or star-shaped calcium pyrophosphate particles.

22. A composition according to claim 20, wherein the gel beads are selected from the group consisting of alginate, gellan gum, gelatin, and collagen.

* * * * *